United States Patent [19]

Urakami et al.

[11] Patent Number: 5,061,711

[45] Date of Patent: Oct. 29, 1991

[54] METHOD OF CURING LIVER DISEASES BY USING PYRROLO QUINOLINE QUINONE TRIESTERS AND NOVEL PYRROLO QUINOLINE QUINONE TRIESTERS

[75] Inventors: Teizi Urakami, Tokyo; Mitsunori Oda; Chieko Itoh, both of Niigata, all of Japan

[73] Assignee: Mitsubishi Gas Chemical Company, Inc., Tokyo, Japan

[21] Appl. No.: 592,266

[22] Filed: Oct. 3, 1990

[30] Foreign Application Priority Data

Oct. 9, 1989 [JP] Japan ................................ 1-262109
Jun. 28, 1990 [JP] Japan ................................ 2-168484

[51] Int. Cl.$^5$ .............................................. A61K 31/44
[52] U.S. Cl. .................................................... 514/292
[58] Field of Search ........................... 514/292; 546/84

[56] References Cited

U.S. PATENT DOCUMENTS 4,898,870 2/1990 Narutomi et al. .................. 514/292

OTHER PUBLICATIONS

J. Org. Chem., 1982, 47, 2833-2837; James A. Gainor and Steven M. Weinreb.
J. Org. Chem., 1985, 50, 1688-1695; James B. Hendrickson and Johannes G. de Vries.

*Primary Examiner*—Stanley J. Friedman
*Attorney, Agent, or Firm*—Wyatt, Gerber, Burke & Badie

[57] ABSTRACT

Disclosed is a method of curing liver diseases by administration of pyrrolo quinoline quinon triesters (PQQ triesters). The PQQ triesters include PQQ triallyl ester and PQQ tribenzyl ester which are novel. The PQQ triesters being ester form, they have no toxicity and can be orally adminstered.

2 Claims, No Drawings

METHOD OF CURING LIVER DISEASES BY USING PYRROLO QUINOLINE QUINONE TRIESTERS AND NOVEL PYRROLO QUINOLINE QUINONE TRIESTERS

TECHNICAL FIELD

The present invention relates to a method for curing liver diseases by using pyrrolo quinoline quinone triesters (hereinafter referred to as "PQQ triesters"). The invention also relates to two novel PQQ triester compounds, PQQ triallyl ester and PQQ tribenzyl ester.

BACKGROUND ART

Liver is an important organ which participates in most of metabolisms and regulation thereof in a living body including metabolization of carbohydrate, protein, lipid, nucleic acid, vitamin, and hormone, production of bilirubin, secretion of bile, detoxification of endogeneous or exogeneous substances by oxidation, reduction and conjugation ° and excretion of them into bile or water-solubilization of them to accelerate excretion into urine. These functions may be damaged by toxic substances, medicines, alcohols, radiation and viruses to cause diseases such as medicinal liver diseases, alcoholic liver diseases, virus-caused hepatitis, fatty liver, jaundice, and the like. If these diseases are protracted, sometimes liver cirrhosis and liver cancer are developed.

However, medicines effective to cure these liver diseases have not yet been developed and at present, treatments therefor are only alimentotherapy and rest cure.

On the other hand, recently, it has been reported that pyrrolo quinoline quinone and pyrrolo quinoline quinone salts (hereinafter generically referred to as "PQQ") found as novel coenzymes of oxido-reductase inhibit liver diseases when administered intraperitoneally. (Japanese Patent Kokai No. 63-192717).

However, this activity was not observed when they are orally administered. (Watanabe et al, "Current Therapeutic Research", Vol. 44, No. 6, pp 896-901 (1988)). Furthermore, it has been clarified that "PQQ" has kidney toxicity (Watanabe et al, "Hiroshima J.Med. Sci.", Vo.1 38, No. 1, pp49-51 (1989)).

Thus, it has been desired to develop medicines which are low in toxicity, especially kidney toxicity, high in membrane permeability and can inhibit liver diseases not only through intraperitoneal administration, but also oral administration.

SUMMARY OF THE INVENTION

It is an object of the present invention to provide a method of curing liver diseases utilizing PQQ triesters. Another object of this invention is to provide novel PQQ triesters.

DISCLOSURE OF THE INVENTION

Liver diseases cause biochemically or histologically peculiar changes such as increase in enzymes of liver such as glutamic acid-oxalacetic acid transaminase (hereinafter referred to as "GOT") and glutamic acid-pyruvic acid transaminase (hereinafter referred to as "GPT") in blood, increase in bilirubin in serum, and necrosis of hepatic cells. Experimental models of hepatitis have been developed for study of liver diseases. Among them, models of liver diseases caused by carbon tetrachloride or D-galactosamine using rats are often utilized.

The sequential steps in liver diseases caused by carbon tetrachloride are believed to be as follows. Carbon tetrachloride is converted to the free radical ($\cdot CCl_3$) by cytochrome P-450 and this free radical bonds to protein of hepatic cell membrane to inhibit cell activity or the free radical accelerates peroxidation reaction of lipid in membrane to change membrane structure. The mechanism of liver diseases caused by D-galactosamine has not yet been clarified, but there is a report that it is caused by production of UDP (uridine diphosphate)-hexamine and deficiency of UTP (uridine triphosphate).

The inventors have conducted intensive research in an attempt to develop medicines having low toxicity, high membrane permeability and inhibitory action on liver diseases not only through intraperitoneal administration, but also through oral administration using models of rat contracting liver disease caused by carbon tetrachloride or D-galactosamine. As a result, it has been found that PQQ triesters are low in toxicity, high in membrane permeability and can markedly inhibit increase of GOT, GPT and total bilirubin through both intraperitoneal administration and oral administration.

According to the present invention, there is provided a method of curing liver diseases by using PQQ triesters including the novel PQQ triallyl ester and PQQ tribenzyl ester.

BEST MODE OF CARRYING OUT THE INVENTION

PQQ triesters used in the method of the present invention are represented by the following formula (I):

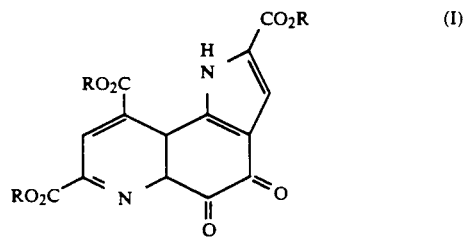

(wherein R represents a lower alkyl group having 1 to carbon atoms, a lower alkenyl group having 2 to 4 carbon atoms or a benzyl group).

Lower alkyl group of R in the formula (I) includes, for example, methyl, ethyl, propyl, isopropyl, butyl, isobutyl, sec-butyl, and tert-butyl groups and lower alkenyl group includes, for example, vinyl, allyl, 1-propenyl, isopropenyl, 1-butenyl, and 2-butenyl groups.

The PQQ triesters in the present invention can be easily produced by allowing PQQ or PQQ salt to react with a halide having group R of the formula (I) or by allowing PQQ or PQQ salt to react with an alcohol by conventional process.

PQQ trimethyl ester is disclosed in Japanese Patent Kokai No. 63-48215, but it has never been known that the compound is effective for curing of liver diseases.

PQQ triallyl ester and PQQ tribenzyl ester are novel compounds. The process for producing these compounds will be explained below.

PQQ triallyl ester of the present invention can be produced by various processes. The presently preferred is a process which comprises allowing a "PQQ" to react with an allyl halide in the presence of a base in an aprotic solvent.

Not only PQQ per se, but also PQQ salts such as sodium salt and potassium salt of PQQ may be used.

As allyl halides, for example, allyl bromide and allyl iodide may be used.

As bases, there may be used, for example, alkali metal hydroxides and carbonates and tertiary amines such as diethylisopropylamine which is difficult to convert to quaternary form.

As aprotic solvents, there may be used, for example, dimethylformamide, hexamethylphosphoryltriamide, dimethyl sulfoxide, dimethylacetamide, and dimethylimidazolidinone.

Reaction can be carried out at room or ordinary temperatures, preferably up to 100° C.

Isolation and purification of PQQ triallyl ester from reaction mixture can be performed by the usual methods such as extraction with solvent, recrystallization and column chromatography.

PQQ tribenzyl ester can also be produced by various processes and preferred is a process which comprises allowing a PQQ to react with a benzyl halide in the presence of a base in an aprotic solvent.

As "PQQ", there may be used not only PQQ per se, but also PQQ salts such as sodium salt of PQQ and potassium salt of PQQ.

As benzyl halides, there may be used, for example, benzyl chloride, benzyl bromide and benzyl iodide.

As bases, there may be used, for example, alkali metal hydroxides and carbonates and tertiary amines such as ethyldiisopropylamine which is difficult to convert to quaternary form.

As aprotic solvents, there may be used, for example, dimethylformamide, hexamethylphosphoryl triamide, dimethyl sulfoxide, dimethylacetamide, and dimethylimidazolidinone.

Reaction can be carried out at room or ordinary temperature, preferably is up to 100° C.

Isolation and purification of PQQ tribenzyl ester from reaction mixture can be performed by usual methods such as extraction with solvent, recrystallization and column chromatography.

The PQQ triesters of the present invention can be administered by either oral administration or non-oral administration. In the case of oral administration, the PQQ triesters may be administered in the usual forms such as capsules, tablets and powders. In the case of non-oral administration, they are administered in the form of injectable liquid. Slow release formulations are also effective.

Although the quantity of the PQQ ester administered varies depending on the condition of a patient, the selected PQQ esters, the method of administration and the like, it is usually 1–100 mg/kg.day, preferably 2–50 mg/kg day. Said PQQ ester can be administered in 1 dose or as 2–3 doses separately in a day.

The active ingredient of the present invention is formulated using optionally surface active agent, vehicle, colorant, preservative, coating aid, and the like. Moreover, it may be used in combination with other medicines.

(Membrane permeability test on PQQ and PQQ triesters)

Permeability of various compounds through capsule of crystal bovine lens was examined in accordance with the method mentioned in "Crystal Lens and Biochemical Mechanism thereof" (pages 436–440) edited by Shuzo Iwata (Medical Aoi Publisher).

Each compound dissolved in 10 mM HEPES buffer (containing 1%DMSO in the case of PQQ triesters) was put in an apparatus for measurement of membrane permeation constant and left to stand for 16 hours at 35 ° C. and then amount of the compound which migrated was measured by ultraviolet absorption (243 nm for PQQ 2Na and 255 nm for PQQ triester) to obtain membrane permeation constant.

As shown in Table 1, membrane permeation constant of PQQ triallyl ester is 3–4 times that of PQQ.2Na and those of PQQ trimethyl ester and PQQ triethyl ester are about 2 times that of PQQ.2Na. Thus, it is recognized that membrane permeability is extremely improved.

TABLE 1

| Compound | Membrane permeation constant ($10^{-7}cm^2 \cdot sec^{-1}$) |
| --- | --- |
| PQQ.2Na | 0.68 ± 0.36 |
| PQQ trimethyl ester | 1.41 ± 0.48 |
| PQQ triethyl ester | 1.22 ± 0.37 |
| PQQ triallyl ester | 2.42 ± 0.60 |

(Acute toxicity test and kidney toxicity test of PQQ and PQQ triesters)

(1) Acute toxicity test:

To male mice SPF-ICR five weeks old (supplied by Japan Charles River Co.) were intraperitoneally administered PQQ.2Na, PQQ trimethyl ester and PQQ triallyl ester at dosages of 40, 80, 160 and 200 mg per kg of body weight of mouse, respectively and they were bred for 14 days at 25° C. One group consisted of 8 mice. For administration, PQQ.2Na was dissolved in physiological saline and PQQ trimethyl ester and PQQ triallyl ester were suspended in 1%Tween 80-containing physiological saline, respectively.

No mice died with administration of 40 mg/kg-mouse of PQQ.2Na, but five mice died with administration of 80 mg and eight mice all died with administration of 160 mg and 200 mg. On the other hand, no mice died with administration of PQQ trimethyl ester and PQQ triallyl ester at any tested level.

Thus, it can be seen that PQQ esters are conspicuously low in toxicity as compared with PQQ.

(2) Kidney toxicity determined by urine test

PQQ.2Na, PQQ trimethyl ester and PQQ triallyl ester were intraperitoneally administered to mice and they were bred in the same manner as in the above acute toxicity test. The doses per kg of body weight of mouse were 20, 40 and 80 mg for PQQ.2Na and 20, 40, 80, 160 and 200 mg for PQQ triesters. Urine was collected every day and glucose concentration was examined using clinical examination reagent (trademark: URIS-TICKS II manufactured by Miles.Sankyo Co.).

As shown in Table 2, glucose was detected in urine of mice to which PQQ.2Na was administered while no glucose was detected in urine of any mouse to which PQQ trimethyl ester or PQQ triallyl ester was administered.

That is, PQQ showed kidney toxicity, but PQQ triesters did not show kidney toxicity.

TABLE 2

| Administration of compound | Elapsed days (day) | | | | | | | | |
| --- | --- | --- | --- | --- | --- | --- | --- | --- | --- |
| | 1 | 2 | 3 | 6 | 7 | 8 | 10 | 13 | 14 |
| No administration | — | — | — | — | — | — | — | — | — |

TABLE 2-continued

| Administration | Elapsed days (day) | | | | | | | | |
|---|---|---|---|---|---|---|---|---|---|
| of compound | 1 | 2 | 3 | 6 | 7 | 8 | 10 | 13 | 14 |
| PQQ.2Na | | | | | | | | | |
| 20 mg/kg | − | − | − | − | − | − | − | − | − |
| 40 mg/kg | 3+ | 4+ | 4+ | 3+ | ± | ± | ± | ± | − |
| 80 mg/kg | 4+ | 4+ | 4+ | 3+ | + | ± | − | − | − |
| PQQ trimethyl ester | | | | | | | | | |
| 20 mg/kg | − | − | − | − | − | − | − | − | − |
| 40 mg/kg | − | − | − | − | − | − | − | − | − |
| 80 mg/kg | − | − | − | − | − | − | − | − | − |
| 160 mg/kg | − | − | − | − | − | − | − | − | − |
| 200 mg/kg | − | − | − | − | − | − | − | − | − |
| PQQ triallyl ester | | | | | | | | | |
| 20 mg/kg | − | − | − | − | − | − | − | − | − |
| 40 mg/kg | − | − | − | − | − | − | − | − | − |
| 80 mg/kg | − | − | − | − | − | − | − | − | − |
| 160 mg/kg | − | − | − | − | − | − | − | − | − |
| 200 mg/kg | − | − | − | − | − | − | − | − | − |

− glucose not detected
± glucose 0.10 g/dl
+ glucose 0.25 g/dl
2+ glucose 0.50 g/dl
3+ glucose 1.00 g/dl
4+ glucose 2.00 g/dl (3) Kidney toxicity determined by blood examination:

PQQ.2Na and PQQ triallyl ester were intraperitoneally administered to mice and they were bred in the same manner as in the acute toxicity test.

After lapse of one day from the administration, the mice were fasted (only water was given) and then after 18 hours, blood was collected and serum was obtained therefrom. Glucose, urea nitrogen and creatinine in the serum were examined by clinical examination reagent (trademark: FUJI DRYCHEMSLIDE manufactured by Fuji Photo Film Co., Ltd.). The results are shown by average value of eight mice in Table 3.

Sharp reduction of glucose and much increase of urea nitrogen and creatinine were seen and kidney toxicity was observed when PQQ·2Na was administered. On the other hand, when PQQ triallyl ester was administered, contents of glucose, urea nitrogen and creatinine were nearly the same as those in the case of administration of no compounds and thus no kidney toxicity was observed.

TABLE 3

| Administration of compound (mg/kg) | Glucose (mg/dl) | Urea nitrogen (mg/dl) | Creatinine (mg/dl) |
|---|---|---|---|
| None | 78 | 20 | 0.4 |
| PQQ.2Na | | | |
| 20 | 70 | 21 | 0.5 |
| 40 | 60 | 110 | 2.3 |
| 80 | 57 | 130 | 3.4 |
| 160 | 35 | 139 | 4.2 |
| PQQ triallyl ester | | | |
| 40 | 42 | 12 | 0.3 |
| 80 | 47 | 12 | 0.2 |
| 160 | 59 | 10 | 0.2 |
| 200 | 64 | 9 | 0.1 |

(4) Kidney toxicity (2) determined by blood examination:

PQQ trimethyl ester was administered to mice and they were bred in the same manner as in the acute toxicity test. The dosage per kg of body weight of mouse was 150, 400 mg and 100 mg.

After lapse of one day from the administration, the mice were fasted (only water was given) and then, after 15 hours, blood was collected and serum was obtained therefrom. Glucose, urea nitrogen and creatinine in the serum were examined by clinical examination reagent (trademark : FUJI DRYCHEMSLIDE manufactured by Fuji Photo Film Co., Ltd.). The results are shown by average value of eight mice in Table 4.

No kidney toxicity was observed even when PQQ trimethyl ester was administered in a dose of 1000 mg/kg(mouse).

TABLE 4

| Administration of compound (mg/kg) | Glucose (mg/dl) | Urea nitrogen (mg/dl) | Creatinine (mg/dl) |
|---|---|---|---|
| None | 93 | 23 | 0.8 |
| PQQ trimethyl ester | | | |
| 150 | 72 | 22 | 0.9 |
| 400 | 55 | 20 | 0.7 |
| 1000 | 60 | 17 | 0.7 |

The following nonlimiting examples show effect of PQQ triesters to inhibit liver diseases and PQQ.triesters as novel compounds.

EXAMPLE 1

Pharmacological activity (1) of PQQ triesters on carbon tetrachloride ($CCl_4$)-induced liver diseases:

Twenty SD rats (male, 7 weeks old, body weight: about 220 g; supplied by Japan Charles River Co.) were divided to four groups (A-D) each consisting of five rats. All rats were fasted for 16 hours and 1.1 ml of a solution containing 1 mg/ml of PQQ trimethyl ester was intraperitoneally administered to the rats of group C and 1.1 ml of a solution containing 1 mg/ml of PQQ triallyl ester was intraperitoneally administered to the rats of group D and after lapse of 40 minutes, the same PQQ triesters in the same dose as above was intraperitoneally administered, respectively. For administration, the PQQ triesters were suspended in physiological saline containing 1 % Tween 80, 1.1 ml of physiological saline was intraperitoneally administered to the rats of group B in place of PQQ triesters. Furthermore, after 20 minutes, 2.2 ml of 10 vol% carbon tetrachloride (solution in olive oil) was administered to stomach of the rats of groups B-D. Neither PQQ triesters nor carbon tetrachloride were administered to the rats of group A.

After 24 hours from administration of carbon tetrachloride, blood was collected from abdominal main artery and serum was obtained by centrifugation therefrom.

GPT, GOT and amount of total bilirubin in the serum were measured by clinical examination reagent (trademark: FUJI DRYCHEMSLIDE manufactured by Fuji Photo Film Co., Ltd.). The results are shown in Table 5 by average value of five rats.

GPT, GOT and amount of total bilirubin which increased by administration of carbon tetrachloride all markedly decreased by administration of PQQ triesters and it can be seen that PQQ triesters have effect to inhibit liver diseases.

TABLE 5

| Group | Administration of PQQ. triesters | Administration of carbon tetrachloride | GPT U/l | GOT U/l | Total bilirubin mg/dl |
|---|---|---|---|---|---|
| A | None | None | 16 | 144 | 0.5 |

TABLE 5-continued

| Group | Administration of PQQ. triesters | Administration of carbon tetra-chloride | GPT U/l | GOT U/l | Total bilirubin mg/dl |
|---|---|---|---|---|---|
| B | None | 1 ml/kg rat | 818 | 3308 | 1.2 |
| C | PQQ trimethyl ester 5 mg/kg rat Twice | 1 ml/kg rat | 505 | 2193 | 0.7 |
| D | PQQ triallyl ester 5 mg/kg rat Twice | 1 ml/kg rat | 371 | 2150 | 0.8 |

EXAMPLE 2

Pharmacological activity (2) of PQQ triesters on carbon tetrachloride ($CCl_4$)-induced liver diseases:

Forty SD rats (male, 7 weeks old, body weight: about 260 g; supplied by Japan Charles River Co.) were divided to eight groups (A-H) each consisting of five rats. All rats were fasted for 18 hours and 1.3 ml of a solution containing 2 mg/ml of PQQ trimethyl ester was intraperitoneally administered to the rats of group C, 1.3 ml of a solution containing 10 mg/ml of PQQ trimethyl ester was intraperitoneally administered to the rats of group D, 1.3 ml of a solution containing 20 mg/ml of PQQ trimethyl ester was intraperitoneally administered to the rats of group E, 1.3 ml of a solution containing 2 mg/ml of PQQ triallyl ester was intraperitoneally administered to the rats of group F, 1.3 ml of a solution containing 10 mg of PQQ triallyl ester was intraperitoneally administered to the rats of group G, and 1.3 ml of a solution containing 20 mg/ml of PQQ triallyl ester was intraperitoneally administered to the rats of group H and furthermore, after lapse of 50 minutes, the same PQQ triesters in the same doses as above were intraperitoneally administered to respective rats. In these cases, the PQQ triesters were suspended in physiological saline containing 1% Tween 80 and administered to the rats. 1.3 ml of physiological saline was intraperitoneally administered to the rats of group B in place of PQQ triesters. Furthermore, after lapse of 20 minutes, 0.6 ml of 12 vol% carbon tetrachloride (solution in olive oil) was intraperitoneally administered to the rats of groups B-H. Neither PQQ triesters nor carbon tetrachloride were administered to the rats of group A.

After 24 hours from administration of carbon tetrachloride, blood was collected from abdominal main artery and serum was obtained by centrifugation therefrom.

GPT, GOD and amount of total bilirubin in the serum were measured by clinical examination reagent (trademark: FUJI DRYCHEMSLIDE manufactured by Fuji Photo Film Co., Ltd.). The results are shown in Table 6 by average value of five rats.

GPT, GOT and amount of total bilirubin which increased by administration of carbon tetrachloride all markedly decreased by administration of PQQ triesters and it can be seen that PQQ triesters have effect to inhibit liver diseases.

TABLE 6

| Group | Administration of triesters | Administration of carbon tetra-chloride | GPT U/l | GOT U/l | Total bilirubin mg/dl |
|---|---|---|---|---|---|
| A | None | None | 16 | 155 | 0.4 |
| B | None | 1 ml/kg rat | 949 | 1970 | 0.9 |
| C | PQQ trimethyl ester 10 mg/kg rat Twice | 1 ml/kg rat | 479 | 1263 | 0.9 |
| D | PQQ trimethyl ester 50 mg/kg rat Twice | 1 ml/kg rat | 645 | 1543 | 0.7 |
| E | PQQ trimethyl ester 100 mg/kg rat Twice | 1 ml/kg rat | 676 | 1605 | 0.8 |
| F | PQQ triallyl ester 10 mg/kg rat Twice | 1 ml/kg rat | 323 | 1186 | 0.7 |
| G | PQQ triallyl ester 50 mg/kg rat Twice | 1 ml/kg rat | 583 | 1270 | 0.7 |
| H | PQQ triallyl ester 100 mg/kg rat Twice | 1 ml/kg rat | 576 | 1563 | 0.8 |

EXAMPLE 3

Pharmacological effect (1) of PQQ triesters on D-galactosamine-induced liver diseases;

Forty SD rats (male 7 weeks old, body weight: about 240 g; supplied by Japan Charles River Co.) were divided to eight groups (A-H) each consisting of five rats. All rats were fasted for 16 hours and 1.2 ml of a solution containing 0.4 mg/ml of PQQ trimethyl ester was intraperitoneally administered to the rats of group C, 1.2 ml of a solution containing 1.0 mg/ml of PQQ trimethyl ester was intraperitoneally administered to the rats of group D, 1.2 ml of a solution containing 2.0 mg/ml of PQQ trimethyl ester was intraperitoneally administered to the rats of group E, 1.2 ml of a solution containing 0.4 mg/ml of PQQ triallyl ester was intraperitoneally administered to the rats of group F, 1.2 ml of a solution containing 1.0 mg/ml of PQQ triallyl ester was intraperitoneally administered to the rats of group G, and 1.2 ml of a solution containing 2.0 mg/ml of PQQ triallyl ester was intraperitoneally administered to the rats of group H and furthermore, after 40 minutes, the same PQQ triesters in the same doses as above were intraperitoneally administered to respective rats. In these cases, the PQQ triesters were suspended in physiological saline containing 1% Tween 80 and administered to the rats. 1.2 ml of physiological saline was intraperitoneally administered to the rats of group B in place of PQQ triesters. Furthermore, after 20 minutes, 1.2 ml of a solution of 2 g of D-galactosamine in 10 ml of physiological saline was subcutaneously injected to the rats of groups B-H. Neither PQQ triesters nor D-galactosamine were administered to the rats of group A.

After 23 hours from administration of D-galactosamine, blood was collected from abdominal main artery and serum was obtained by centrifugation therefrom.

GPT, GOT and amount of total bilirubin in the serum were measured by clinical examination reagent (trademark: FUJI DRYCHEMSLIDE manufactured by Fuji Photo Film Co., Ltd.). The results are shown in Table 7 by average value of five rats.

GPT, GOT and amount of total bilirubin which increased by administration of D-galactosamine all markedly decreased by administration of PQQ triesters and it can be seen that PQQ triesters have effect to inhibit liver diseases.

TABLE 7

| Group | Administration of PQQ triesters | Administration of D-galactosamine | GPT U/l | GOT U/l | Total bilirubin mg/dl |
|---|---|---|---|---|---|
| A | None | None | 27 | 191 | 0.6 |
| B | None | 1 g/kg rat | 552 | 1067 | 1.0 |
| C | PQQ trimethyl ester 2 mg/kg rat Twice | 1 g/kg rat | 447 | 970 | 0.9 |
| D | PQQ trimethyl ester 5 mg/kg rat Twice | 1 g/kg rat | 182 | 544 | 0.5 |
| E | PQQ trimethyl ester 10 mg/kg rat Twice | 1 g/kg rat | 388 | 833 | 0.7 |
| F | PQQ triallyl ester 2 mg/kg rat Twice | 1 g/kg rat | 538 | 1132 | 0.8 |
| G | PQQ triallyl ester 5 mg/kg rat Twice | 1 g/kg rat | 322 | 648 | 0.8 |
| H | PQQ triallyl ester 10 mg/kg rat Twice | 1 g/kg rat | 120 | 480 | 0.6 |

EXAMPLE 4

Pharmacological effect (2) of PQQ triesters on D-galactosamine-induced liver diseases:

Forty SD rats (male, 7 weeks old, body weight: about 260 g; supplied by Japan Charles River Co.) were divided to eight groups (A-H) each consisting of five rats. All rats were fasted for 18 hours and 1.3 ml of a solution containing 1 mg/ml of PQQ trimethyl ester was orally administered to the rats of group C, 1.3 ml of a solution containing 2 mg/ml of PQQ trimethyl ester was orally administered to the rats of group D, 1.3 ml of a solution containing 3 mg/ml of PQQ trimethyl ester was orally administered to the rats of group E, 1.3 ml of a solution containing 1 mg/ml of PQQ triallyl ester was orally administered to the rats of group F, 1.3 ml of a solution containing 2 mg/ml of PQQ triallyl ester was orally administered to the rats of group G, and 1.3 ml of a solution containing 3 mg/ml of PQQ triallyl ester was orally administered to the rats of group H and furthermore, after lapse of 40 minutes, the same PQQ triesters in the same doses as above were orally administered to respective rats. In these cases, the PQQ triesters were suspended in physiological saline containing 1% Tween 80 and administered to the rats. 1.3 ml of physiological saline was orally administered to the rats of group B in place of PQQ triesters. Furthermore, after lapse of 20 minutes, 1.3 ml of a solution of d-galactosamine in 10 ml of physiological saline was intraperitoneally administered to the rats of groups B-H. Neither PQQ triesters nor D-galactosamine were administered to the rats of group A.

After 23 hours from administration of D-galactosamine, blood was collected from abdominal main artery and serum was obtained by centrifugation therefrom.

GPT, GOT and amount of total bilirubin in the serum were measured by clinical examination reagent (trademark: FUJI DRYCHEMSLIDE manufactured by Fuji Photo Film Co., Ltd.). The results are shown in Table 8 by average value of five rats.

GPT, GOT and amount of total bilirubin which increased by administration of D-galactosamine all markedly decreased by administration of PQQ triesters and it can be seen that PQQ triesters have effect to inhibit liver diseases.

TABLE 8

| Group | Administration of PQQ triesters | Administration of D-galactosamine | GPT U/l | GOT U/l | Total bilirubin mg/dl |
|---|---|---|---|---|---|
| A | None | None | 22 | 124 | 0.5 |
| B | None | 1 g/kg rat | 1560 | 2542 | 1.4 |
| C | PQQ trimethyl ester 5 mg/kg rat Twice | 1 g/kg rat | 431 | 926 | 0.8 |
| D | PQQ trimethyl ester 10 mg/kg rat Twice | 1 g/kg rat | 330 | 540 | 0.7 |
| E | PQQ trimethyl ester 15 mg/kg rat Twice | 1 g/kg rat | 701 | 1260 | 1.0 |
| F | PQQ triallyl ester 5 mg/kg rat Twice | 1 g/kg rat | 619 | 1409 | 1.1 |
| G | PQQ triallyl ester 10 mg/kg rat Twice | 1 g/kg rat | 570 | 1184 | 0.9 |
| H | PQQ triallyl ester 15 mg/kg rat Twice | 1 g/kg rat | 593 | 1742 | 1.0 |

EXAMPLE 5

To a solution of 1 g of PQQ in 50 ml of dry dimethylformamide were added 9 g of potassium carbonate.

To this suspension were added 15 ml of allyl bromide and reaction was allowed to proceed at 25° C, for 7 days with stirring in nitrogen stream to obtain a reaction mixture.

The whole of the reaction mixture was mixed with 200 ml of 3N aqueous hydrochloric acid solution. To this mixed solution were added 30 ml of chloroform. carbon tetrachloride (3:2 volumetric ratio), the mixture was shaken and chloroform-carbon tetrachloride layer was recovered. This extraction operation was carried out three times.

The liquid of recovered chloroform-carbon tetrachloride layer was washed with water and then 5 g of sodium sulfate were added thereto, followed by dehydration.

Sodium sulfate was removed from the liquid by filtration, followed by concentration under reduced pressure.

The residue was dissolved in 20 ml of ethyl ether and left to stand at 5° C. for 10 hours to precipitate crystal, which was recovered by filtration and washed with ethyl ether.

This crystal was dried to obtain 0.751 g of PQQ triallyl ester.

The filtrate was concentrated to dryness and subjected to silica gel thin-layer chromatography (developer ethyl ether: chloroform=1 : 9) to recover 0.060 g of PQQ triallyl ester.

Amount of the resulting PQQ triallyl ester was 0.811 g and yield of PQQ triallyl ester based on PQQ was 59 mol%.

(1) Elemental analysis : $C_{23}H_{18}O_8N_2$ (MW 450.40)

Calcd. (%):C; 61.33, H; 4.03, N; 6.22

Found (%):C; 60.98, H; 4.21, N; 5.97

(2) Melting point: 142–144° C.

(3) Solubility: Very soluble in methanol, ethanol and acetone and hardly soluble in water.

(4) Hydrogen nuclear magnetic resonance spectrum (in DMSO-$d_6$ with tetramethylsilane as internal standard): $\delta$4.75–5.10(m, 6H), 5.2–6.3(m, 9H), 7.35(d, J=1.5Ht, 1H), 8.73(s, 1H), 13.00(br, 1H)ppm.

(5) Electronic spectrum: $\lambda$max($CH_3OH$) 208, 253, 376 nm.

(6) Infrared absorption spectrum (KBr): $\nu$max3100$^w$, 1700$^s$, 1680$^s$, 1190$^{sh}$, 1170$^{vs}$, 1105$^m$, 975$^w$, 920$^m$cm$^{-1}$.

EXAMPLE 6

To a solution of 600 mg of PQQ in 20 ml of dry dimethylformamide were added 1.38 g of potassium carbonate. To this suspension were added 3.08 g of benzyl bromide and reaction was allowed to proceed at 25° C. for 5 days with stirring in nitrogen stream.

The whole of the resulting reaction mixture was mixed with 100 ml of 2N aqueous hydrochloric acid solution. To this mixed solution were added 30 ml of chloroform.carbon tetrachloride.ethyl acetate (1:1:1 volumetric ratio), the mixture was shaken and chloroform-carbon tetrachloride-ethyl acetate layer was recovered. This extraction operation was carried out three times. This chloroform-carbon tetrachloride-ethyl acetate solution was washed with 0.1 N hydrochloric acid and water and then 5 g of sodium sulfate were added, followed by dehydration.

Sodium sulfate was removed by filtration, followed by concentration under reduced pressure. The residue was subjected to silica gel column chromatography (developer ethyl ether : chloroform =5 : 95) to obtain fraction of crude PQQ tribenzyl ester, which was concentrated to dryness. The residue was dissolved in 20 ml of ethyl ether and left to stand at 5° C. for 10 hours to precipitate crystal and this crystal was dried to obtain 520 mg of PQQ tribenzyl ester. Yield of PQQ tribenzyl ester based on PQQ was 48 mol%.

The resulting compound had a melting point of 233–236° C. and was very soluble in methanol, ethanol, chloroform and acetone and hardly soluble Characteristics of the resulting PQQ tribenzyl ester are shown below.

(1) Elemental analysis: $C_{35}H_{24}N_2O_8$ (MW 600.59)

Calcd. (%):C; 70.00, H; 4.03 N; 4.66

Found (%):C; 70.30, H; 3.85, N; 4.82

(2) Melting point: 233–236° C.

(3) Solubility: Very soluble in methanol, ethanol, chloroform and acetone and hardly soluble in water.

(4) Hydrogen nuclear magnetic resonance spectrum (in DMSO-$d_6$ with tetramethylsilane as internal standard): $\delta$5.39 (s, 2H), 5.43(s, 2H), 5.47(s, 2H), 7.4(m, 16H), 8.65(s, 1H), 12.56(br, 1H)ppm.

(5) Electronic spectrum: $\lambda$max($CH_{30}H$) 206, 254 378 nm.

(6) Infrared absorption spectrum (KBr): $\nu$max 3020$^w$, 1700$^{sh}$, 1780$^{vs}$, 1765$^{vs}$, 1365$^m$, 1230$^{vs}$, 1180$^{vs}$, 970$^w$, 830$^w$, 740$^s$, 685$^s$ cm$^{-1}$.

We claim:

1. A method for inhibiting increase of glutamic acid-oxalacetic acid transaminase, glutamic acid-pyruric acid transaminase and tot la bilirubin in a patient in need of such inhibition which comprises administer ting to said patient an amount which is capable of effecting such inhibition of a compound represented by the formula (I)

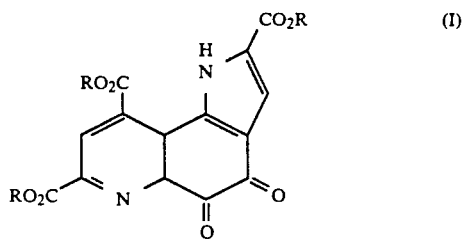

wherein R represents a lower alkyl group having 1 to 4 carbon atoms, a lower alkenyl group having 2 to 4 carbon atoms or a benzyl group.

2. The method according to claim 4, wherein the PQQ triester is PQQ trimethyl ester, PQQ triethyl ester, PQQ triallyl ester or PQQ tribenzyl ester.

* * * * *